(12) United States Patent
Wilhelm et al.

(10) Patent No.: US 9,918,742 B2
(45) Date of Patent: Mar. 20, 2018

(54) MEASURING SKELETAL DISTRACTION

(75) Inventors: Hoa La Wilhelm, Arlington, TN (US);
Gene Edward Austin, Bartlett, TN (US)

(73) Assignee: Smith & Nephew, Inc., Memphis, TN (US)

( * ) Notice: Subject to any disclaimer, the term of this patent is extended or adjusted under 35 U.S.C. 154(b) by 1032 days.

(21) Appl. No.: 13/440,166

(22) Filed: Apr. 5, 2012

(65) Prior Publication Data

US 2012/0296234 A1 Nov. 22, 2012

Related U.S. Application Data

(60) Provisional application No. 61/486,483, filed on May 16, 2011.

(51) Int. Cl.
| | |
|---|---|
| *A61B 5/103* | (2006.01) |
| *A61B 17/66* | (2006.01) |
| *A61B 17/72* | (2006.01) |
| *A61B 5/00* | (2006.01) |
| *A61B 5/107* | (2006.01) |
| *A61B 17/62* | (2006.01) |

(52) U.S. Cl.
CPC .......... *A61B 17/66* (2013.01); *A61B 5/0031* (2013.01); *A61B 17/7216* (2013.01); *A61B 5/1072* (2013.01); *A61B 5/4504* (2013.01); *A61B 5/6878* (2013.01); *A61B 17/62* (2013.01)

(58) Field of Classification Search
CPC ... A61B 5/4504; A61B 5/0031; A61B 5/1072; A61B 5/6878; A61B 17/7216; A61B 17/62; A61B 17/66

USPC .......................................................... 600/587
See application file for complete search history.

(56) References Cited

U.S. PATENT DOCUMENTS

| | | | |
|---|---|---|---|
| 3,713,148 A | 1/1973 | Cardullo et al. | |
| 3,727,209 A | 4/1973 | White et al. | |
| 4,096,477 A | 6/1978 | Epstein et al. | |
| 4,242,663 A | 12/1980 | Slobodin | |
| 4,294,263 A * | 10/1981 | Hochman | ............ A61B 5/0059 200/61.02 |

(Continued)

FOREIGN PATENT DOCUMENTS

| | | |
|---|---|---|
| DE | 19855254 A1 | 6/2000 |
| EP | 1099415 A1 | 5/2001 |

(Continued)

OTHER PUBLICATIONS

Mendes, et al., "IntelliJoint System for monitoring displacement in biologic system", Biomed Bytes 2002 (4), pp. 69-70.

(Continued)

*Primary Examiner* — Sean Dougherty
*Assistant Examiner* — Patrick Fernandes
(74) *Attorney, Agent, or Firm* — Fish & Richardson P.C.

(57) ABSTRACT

In one aspect, a method includes transmitting an interrogation signal. A first signal transmitted in response to the interrogation signal is detected, the first signal being transmitted by a first transponder arranged to move with a first bone fragment. A second signal transmitted in response to the interrogation signal is detected, the second signal being transmitted by a second transponder arranged to move with a second bone fragment. A distance between the bone fragments is determined using the detected signals.

19 Claims, 9 Drawing Sheets

(56) References Cited

U.S. PATENT DOCUMENTS

| | | | |
|---|---|---|---|
| 4,481,428 A | 11/1984 | Charlot | |
| 4,510,495 A | 4/1985 | Sigrimis et al. | |
| 5,127,913 A | 7/1992 | Thomas | |
| 5,423,334 A | 6/1995 | Jordan | |
| 5,626,630 A | 5/1997 | Markowitz et al. | |
| 5,681,313 A | 10/1997 | Diez | |
| 5,704,939 A | 1/1998 | Justin | |
| 5,720,746 A | 2/1998 | Soubeiran | |
| 5,961,553 A | 10/1999 | Coty et al. | |
| 5,976,138 A | 11/1999 | Baumgart | |
| 6,261,247 B1* | 7/2001 | Ishikawa et al. | 600/587 |
| 6,369,694 B1 | 4/2002 | Mejia | |
| 6,524,313 B1* | 2/2003 | Fassier et al. | 606/63 |
| 6,535,109 B1* | 3/2003 | Mandavi | G06K 7/10059 340/10.2 |
| 6,658,300 B2 | 12/2003 | Govari et al. | |
| 6,730,087 B1* | 5/2004 | Butsch | 606/57 |
| 6,755,862 B2 | 6/2004 | Keynan | |
| 6,958,677 B1* | 10/2005 | Carter | 340/10.1 |
| 7,001,346 B2 | 2/2006 | White | |
| 7,060,075 B2* | 6/2006 | Govari et al. | 606/98 |
| 7,135,022 B2 | 11/2006 | Kosashvili et al. | |
| 7,218,232 B2 | 5/2007 | DiSilvestro et al. | |
| 7,256,695 B2 | 8/2007 | Hamel et al. | |
| 7,333,013 B2 | 2/2008 | Berger | |
| 7,474,223 B2 | 1/2009 | Nycz et al. | |
| 7,666,184 B2 | 2/2010 | Stauch | |
| 7,753,915 B1 | 7/2010 | Eksler | |
| 7,932,825 B2 | 4/2011 | Berger | |
| 7,981,025 B2 | 7/2011 | Pool | |
| 8,034,054 B2 | 10/2011 | Griggs | |
| 8,137,349 B2 | 3/2012 | Soubeiran | |
| 8,449,543 B2 | 5/2013 | Pool | |
| 8,715,282 B2 | 5/2014 | Pool | |
| 2004/0008123 A1 | 1/2004 | Carrender et al. | |
| 2004/0023623 A1 | 2/2004 | Stauch | |
| 2004/0138663 A1 | 7/2004 | Kosashvili | |
| 2004/0153344 A1 | 8/2004 | Bui et al. | |
| 2004/0176754 A1* | 9/2004 | Island | A61B 18/203 606/9 |
| 2005/0012617 A1 | 1/2005 | DiSilvestro et al. | |
| 2005/0131397 A1 | 6/2005 | Levin | |
| 2005/0247319 A1 | 11/2005 | Berger | |
| 2005/0261779 A1 | 11/2005 | Meyer | |
| 2006/0004459 A1 | 1/2006 | Hazebrouck | |
| 2006/0043178 A1 | 3/2006 | Tethrake et al. | |
| 2006/0142656 A1 | 6/2006 | Malackowski et al. | |
| 2006/0145871 A1 | 7/2006 | Donati et al. | |
| 2006/0181393 A1* | 8/2006 | Raphaeli | G01S 13/44 340/10.1 |
| 2006/0196277 A1 | 9/2006 | Allen et al. | |
| 2006/0235424 A1 | 10/2006 | Vitale et al. | |
| 2006/0247773 A1 | 11/2006 | Stamp | |
| 2006/0293683 A1 | 12/2006 | Stauch | |
| 2007/0233065 A1* | 10/2007 | Donofrio et al. | 606/61 |
| 2007/0265690 A1 | 11/2007 | Lichtenstein et al. | |
| 2008/0033436 A1 | 2/2008 | Song et al. | |
| 2008/0094275 A1* | 4/2008 | Laroche | G01S 13/874 342/126 |
| 2008/0108995 A1 | 5/2008 | Conway | |
| 2008/0119856 A1 | 5/2008 | Gotfried | |
| 2008/0170473 A1* | 7/2008 | Kaiser et al. | 367/140 |
| 2008/0198001 A1* | 8/2008 | Sarma | G06Q 10/087 340/539.1 |
| 2008/0294258 A1 | 11/2008 | Revie et al. | |
| 2009/0036165 A1* | 2/2009 | Brede | 455/558 |
| 2009/0076597 A1 | 3/2009 | Dahlgren | |
| 2009/0112207 A1 | 4/2009 | Walker et al. | |
| 2009/0112262 A1 | 4/2009 | Pool | |
| 2009/0131838 A1 | 5/2009 | Fotiadis et al. | |
| 2009/0222050 A1 | 9/2009 | Wolter et al. | |
| 2009/0254088 A1 | 10/2009 | Soubeiran | |
| 2009/0270728 A1* | 10/2009 | Da Silva | A61B 5/4869 600/437 |
| 2010/0049204 A1 | 2/2010 | Soubeiran | |
| 2010/0152584 A1 | 6/2010 | Ariav et al. | |
| 2010/0228167 A1 | 9/2010 | Ilovich | |
| 2011/0060336 A1 | 3/2011 | Pool et al. | |
| 2011/0137347 A1 | 6/2011 | Hunziker | |
| 2011/0196435 A1 | 8/2011 | Forsell | |
| 2011/0221633 A1* | 9/2011 | Schramm et al. | 342/394 |
| 2011/0230883 A1 | 9/2011 | Zahrly | |
| 2011/0238126 A1 | 9/2011 | Soubeiran | |
| 2012/0130428 A1 | 5/2012 | Hunziker | |
| 2012/0179215 A1 | 7/2012 | Soubeiran | |
| 2012/0209269 A1 | 8/2012 | Pool | |
| 2012/0296234 A1 | 11/2012 | Wilhelm | |
| 2013/0072932 A1 | 3/2013 | Stauch | |

FOREIGN PATENT DOCUMENTS

| | | |
|---|---|---|
| EP | 1704893 A1 | 9/2006 |
| EP | 1764050 A2 | 3/2007 |
| EP | 2173267 | 2/2009 |
| EP | 2151208 A2 | 2/2010 |
| EP | 2380514 A1 | 10/2011 |
| WO | WO1996026678 A1 | 9/1996 |
| WO | WO1997014367 A1 | 4/1997 |
| WO | WO1997020512 A1 | 6/1997 |
| WO | WO2000032124 A1 | 6/2000 |
| WO | WO2001024697 A1 | 4/2001 |
| WO | WO2003044556 A2 | 5/2003 |
| WO | WO2004045431 A1 | 6/2004 |
| WO | WO2006113660 A1 | 10/2006 |
| WO | WO2007061890 A2 | 5/2007 |
| WO | WO2008015679 A3 | 4/2009 |
| WO | WO2013126027 A1 | 8/2013 |

OTHER PUBLICATIONS

SRI Consulting, "RFID Technologies", 2004; and Silicon Chip Online, "RFID Tags—How They Work." reprinted from http://www.siliconchip.com.au/cms/A30750/article.html.

Global market for RFID in healthcare 2006-2016 by value: Source: IDTechEx, RFID in Healthcare 2006-2016, May 1, 2006.

Healthcare RFID Medical Microchip, Yenra, Apr. 30, 2003, reprinted from http://www.yenra.com/healthcare-rfid-medical-microchip/.

Verichip System, Product of VeriChip Corp., reprinted from http://www.verichipcorp.com/content/solutions/verichip reprinted on Apr. 26, 2011.

Sub-dermal RFID, Yenra, Sep. 25, 2003, reprinted from http://www.yenra.com/subdermalrfid/.

Clyde Church, "Radio Frequency Identification (RFID) Tracking of Orthopaedic Inventories Fact or Fiction, Today and Tomorrow," BONE Zone, Spring 2004, pp. 35-40.

Luis Figarella, Kirk Kikirekov, Heinrich Oehlmann, Radio Frequency Identification (RFID) in Health Care, Benefits, Limitations, Recommendations, A Health Industry Business Communications Council HIBCC White Paper (2006).

Alex Macario; Dean Morris; Sharon Morris "Initial Clinical Evaluation of a Handheld Device for Detecting Retained Surgical Gauze Sponges Using Radiofrequency Identification Technology" Arch Surg., 2006; 141:659-662.

Patricia Kaeding "RFID medical devices—Opportunities and challenges," Published Oct. 19, 2005, Wisconsin Technology Network, http://wistechnology.com.

"Can RFID Tags Work Inside Metal?," Xerafy, 2010 (6 pages).

International Preliminary Report on Patentability for International Application No. PCT/US2012/038248, dated Nov. 28, 2013.

International Preliminary Report on Patentability for International Application No. PCT/US2012/032340, dated Nov. 19, 2013.

International Search Report and Written Opinion for International Application No. PCT/US2012/032340, dated Sep. 28, 2012.

Office Action for U.S. Appl. No. 13/109,478, dated Jan. 15, 2013.

International Search Report and Written Opinion for International Application No. PCT/US2011/028764, dated Nov. 23, 2011, 11 pages.

(56) References Cited

OTHER PUBLICATIONS

Office Action for U.S. Appl. No. 14/330,563, dated Apr. 29, 2015.
Office Action for U.S. Appl. No. 14/330,563, dated Jan. 1, 2016.

* cited by examiner

Change since previous measurement:

0.5 mm — 74

Total increase in length: 6.5 mm — 75

Amount remaining to be lengthened: 3.5 mm — 76

Next Scheduled Measurement: 7:00 pm — 77

FIG. 5

MEASURING SKELETAL DISTRACTION

CROSS-REFERENCE TO RELATED APPLICATIONS

This application claims priority to and the full benefit of U.S. Provisional Application Ser. No. 61/486,483, filed May 16, 2011, and titled "Measuring Skeletal Distraction," the entire contents of which are incorporated herein by reference.

TECHNICAL FIELD

This disclosure relates to measuring skeletal distraction.

BACKGROUND

To increase the length of a bone, devices internal or external to a patient can be used to gradually separate bone fragments until a desired length is achieved. The rate at which the bone fragments are separated and the total separation distance are often important to the outcome for the patient.

SUMMARY

In a general aspect, a system for measuring skeletal distraction includes at least two transponders, a limb-lengthening device or a fixation device, and a transceiver for communicating with the transponders. Information from the transponders is used to determine positions of bone fragments coupled to the limb-lengthening device or the fixation device.

In another general aspect, a method includes: transmitting an interrogation signal; detecting a first signal transmitted in response to the interrogation signal, the first signal being transmitted by a first transponder arranged to move with a first bone fragment; detecting a second signal transmitted in response to the interrogation signal, the second signal being transmitted by a second transponder arranged to move with a second bone fragment; and determining a distance between the bone fragments using the detected signals.

Implementations may include one or more of the following features. For example, the first transponder is a passive RFID tag and the second transponder is a passive RFID tag. The first transponder is located within the first bone fragment and the second transponder is located within the second bone fragment. The first transponder and the second transponder are attached to a subcutaneous bone-lengthening device. Determining the distance between the bone fragments using the detected signals includes determining the distance based on (i) a first delay between transmitting the interrogation signal and detecting the first signal and (ii) a second delay between transmitting the interrogation signal and detecting the second signal. Determining the distance between the bone fragments using the detected signals includes determining the distance using a length based on the first delay and a length based on the second delay. Transmitting an interrogation signal includes transmitting the interrogation signal at each of a plurality of locations. Detecting a first signal transmitted in response to the interrogation signal includes detecting, for each transmission of the interrogation signal, a corresponding first response signal from the first transponder. Detecting a second signal transmitted in response to the interrogation signal includes detecting, for each transmission of the interrogation signal, a corresponding second response signal from the second transponder. Determining the distance between the bone fragments using the detected signals includes: measuring delays between each transmission of the interrogation signal and detection of the corresponding first response signal; identifying the shortest delay of the measured delays; determining a related delay between the transmission of the interrogation signal that resulted in the shortest delay and detection of the corresponding second response signal; and determining a distance between the bone fragments using the shortest delay and the related delay. Transmitting an interrogation signal at each of a plurality of locations is performed by an extracutaneous device while the extracutaneous device is moved relative to the first bone fragment and the second bone fragment.

In another general aspect, a method includes: increasing a distance between a first bone fragment and a second bone fragment, a first transponder being coupled to the first bone fragment and a second transponder being coupled to the second bone fragment; after increasing the distance, causing a device to transmit a wireless interrogation signal; and while the device transmits the wireless interrogation signal, moving the device relative to the first bone fragment and the second bone fragment such that, at each of a plurality of locations, the interrogation signal is received by the first transponder and the second transponder, and signals produced by the first transponder and the second transponder in response to the interrogation signal are detected by the device.

Implementations may include one or more of the following features. For example, increasing the distance includes increasing the distance using an external fixation device. The device is a cellular phone.

In another general aspect, a system includes: a bone-lengthening device; a first transponder and a second transponder, the transponders being coupled to the bone-lengthening device and spaced apart from each other along a length of the bone-lengthening device, the transponders each being operable to transmit a radio-frequency signal in response to an interrogation signal; and a reader including a radio-frequency transceiver operable to transmit an interrogation signal and detect responsive signals from the first transponder and the second transponder, one or more processing devices, and one or more storage devices storing instructions that are operable, when executed by the one or more processing devices, to cause the one or more processing devices to perform operations including: causing the transceiver to transmit the interrogation signal and detect the response signals from the first transponder and the second transponder, determining delays between the transmission of the interrogation signal and detection of the response signals from the first transponder and the second transponder, and determining a distance spanned by the transponders based on the delays.

Implementations may include one or more of the following features. For example, the operations include: accessing a stored distance, determining a difference between the determined distance and the stored distance, and indicating the difference on a user interface. The bone-lengthening device is a telescoping intramedullary nail. The first transponder is a passive RFID tag and the second transponder is a passive RFID tag. The bone-lengthening device has a longitudinal axis, and the first transponder and the second transponder are attached to the bone-lengthening device at different locations spaced apart along the longitudinal axis of the bone-lengthening device. The reader is a cellular phone. The operations include storing the distance in association with a time or date that the measurement occurred.

The operations include transmitting the distance to a server system. The operations include determining that the distance does not satisfy a threshold, and in response to determining that the distance does not satisfy the threshold, providing an alarm.

In another general aspect, a system includes: an external fixation device; a first transponder and a second transponder, the transponders being configured to be coupled to different bone fragments, the transponders each being operable to transmit a radio-frequency signal in response to an interrogation signal; and a reader including a radio-frequency transceiver operable to transmit an interrogation signal and detect responsive signals from the first transponder and the second transponder, one or more processing devices, and one or more storage devices storing instructions that are operable, when executed by the one or more processing devices, to cause the one or more processing devices to perform operations including: causing the transceiver to transmit the interrogation signal and detect the response signals from the first transponder and the second transponder, determining delays between the transmission of the interrogation signal and detection of the response signals from the first transponder and the second transponder, and determining a distance spanned by the transponders based on the delays.

Implementations may include one or more of the following features. For example, determining the distance spanned by the transponders includes determining a distance between bone fragments coupled to the bone-lengthening device. Determining delays between the transmission of the interrogation signal and detection of the response signals from the first transponder and the second transponder includes: determining a first delay between the transmission of the interrogation signal and detection of a first response signal transmitted by the first transponder in response to the interrogation signal; and determining a second delay between the transmission of the interrogation signal and detection of a second response signal transmitted by the second transponder in response to the interrogation signal. Determining the distance spanned by the transponders based on the delays includes determining the distance using a length determined based on the first delay and a length determined based on the second delay.

Causing the transceiver to transmit the interrogation signal and detect the response signals from the first transponder and the second transponder includes causing the transceiver to: transmit the interrogation signal at each of a plurality of locations; detect, for each transmission of the interrogation signal, a corresponding first response signal from the first transponder; and detect, for each transmission of the interrogation signal, a corresponding second response signal from the second transponder. Determining delays between the transmission of the interrogation signal and detection of the response signals from the first transponder and the second transponder includes: determining delays between each transmission of the interrogation signal and detection of the corresponding first response signal; identifying a shortest delay of the measured delays; and determining a related delay between the transmission of the interrogation signal that resulted in the shortest delay and detection of the corresponding second response signal. Determining the distance spanned by the transponders based on the delays includes determining the distance using the shortest delay and the related delay. The reader is an extracutaneous device, and causing the transceiver to transmit the interrogation signal and detect the response signals from the first transponder and the second transponder includes causing the reader to transmit the interrogation signal at each of a plurality of locations while the reader is moved relative to the first transponder and the second transponder.

In another general aspect, an apparatus includes a radio-frequency transceiver that is operable to transmit an interrogation signal and detect responsive signals from a first transponder and a second transponder when the first transponder and the second transponder are coupled to different fragments of a bone. The apparatus includes one or more processing devices and one or more storage devices storing instructions that are operable, when executed by the one or more processing devices, to cause the one or more processing devices to perform a variety of operations. The operations include causing the transceiver to transmit the interrogation signal and detect response signals from the first transponder and the second transponder. The operations include determining delays between the transmission of the interrogation signal and detection of the response signals from the first transponder and the second transponder, and determining a change in a length of the bone based on the delays.

Implementations may include one or more of the following features. For example, the apparatus includes a cellular phone. The operations include storing the change in a length of the bone in association with a time or date that the measurement occurred. The operations include transmitting the change in the length of the bone to a server system. The operations include determining that the change in the length of the bone does not satisfy a threshold and, in response to determining that the change in the length of the bone does not satisfy the threshold, providing an alarm. Determining delays between the transmission of the interrogation signal and detection of the response signals from the first transponder and the second transponder includes determining a first delay between the transmission of the interrogation signal and detection of a first response signal transmitted by the first transponder in response to the interrogation signal and determining a second delay between the transmission of the interrogation signal and detection of a second response signal transmitted by the second transponder in response to the interrogation signal. Determining the change in the length of the bone based on the delays includes determining the change in length of the bone using a length determined based on the first delay and a length determined based on the second delay.

Causing the transceiver to transmit the interrogation signal and detect the response signals from the first transponder and the second transponder includes causing the transceiver to: transmit the interrogation signal at each of a plurality of locations; detect, for each transmission of the interrogation signal, a corresponding first response signal from the first transponder; and detect, for each transmission of the interrogation signal, a corresponding second response signal from the second transponder. Determining delays between the transmission of the interrogation signal and detection of the response signals from the first transponder and the second transponder includes: determining delays between each transmission of the interrogation signal and detection of the corresponding first response signal; identifying a shortest delay of the measured delays; and determining a related delay between the transmission of the interrogation signal that resulted in the shortest delay and detection of the corresponding second response signal. Determining the change in the length of the bone based on the delays includes determining the change in the length of the bone using the shortest delay and the related delay. The apparatus is an extracutaneous device, and causing the transceiver to transmit the interrogation signal and detect the response signals from the first transponder and the second transponder includes causing the apparatus to transmit the interrogation signal at each of a plurality of locations while the apparatus is moved relative to the first transponder and the second transponder.

The details of one or more implementations are set forth in the accompanying drawings and the description below. Other features, objects, and advantages of the disclosure will be apparent from the description and drawings.

BRIEF DESCRIPTION OF THE DRAWINGS

FIG. 5 is diagram illustrating a user interface of the reader.

DETAILED DESCRIPTION

Figure 1:
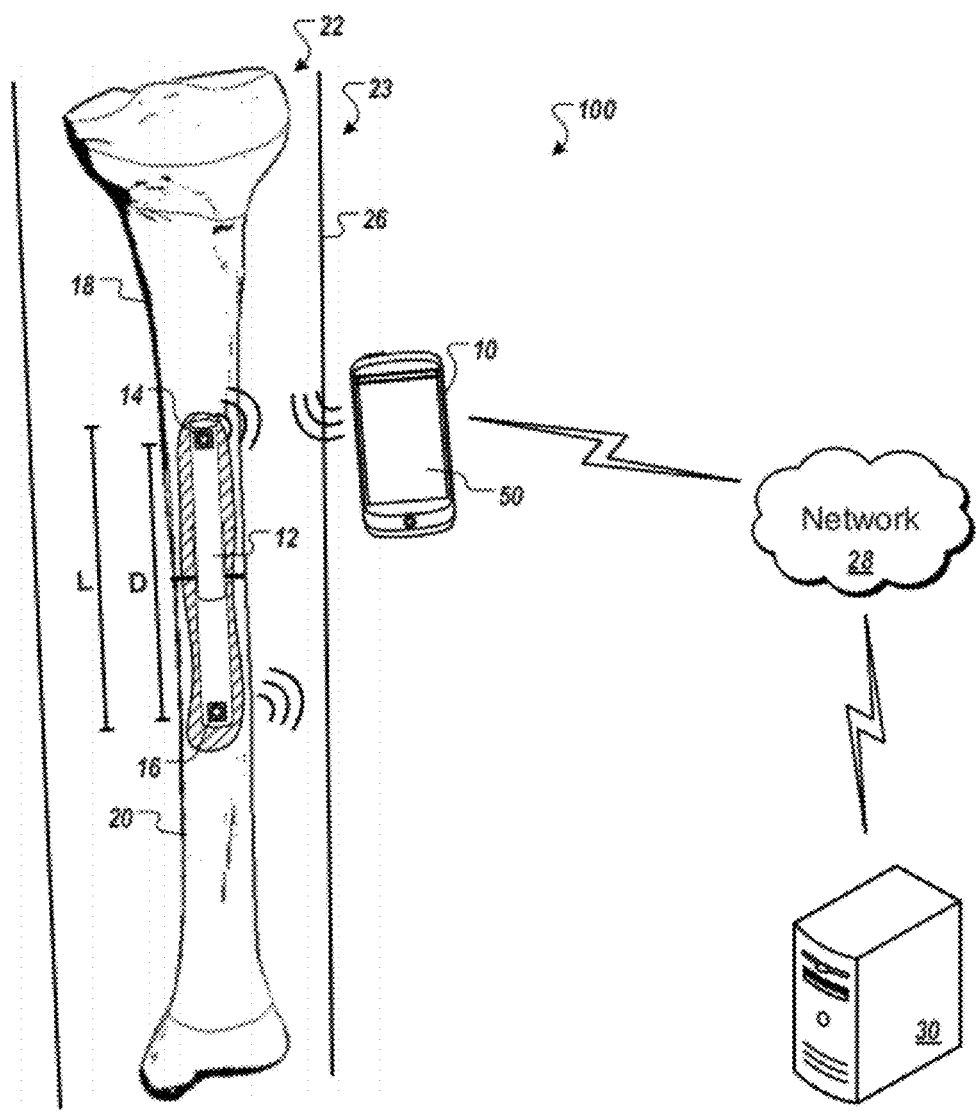
FIG. 1 is a perspective cutaway view of a system for measuring skeletal distraction.

Referring to FIG. 1, a system 100 that can be used to measure skeletal distraction includes a Radio Frequency Identification (RFID) tag reader 10, an intramedullary nail 12, and two radio-frequency transponders 14, 16 attached to the nail 12 and spaced apart along a length, L, of the nail 12. In use, the nail 12 is located in the medullary cavity of two bone fragments 18, 20 of a bone 22, for example, a tibia of a patient's leg 23. The nail 12 is a bone-lengthening device, for example, an intramedullary skeletal kinetic distractor (ISKD) manufactured by Orthodyne, is configured to extend in increments over time, gradually separating the bone fragments 18, 20 and lengthening the bone 22. The transponders 14, 16 are attached to the nail 12, spaced apart along the length of the nail 12. As the nail 12 separates the bone fragments 18, 20, one transponder 14 moves with one bone fragment 18, and the other transponder 16 moves with the other bone fragment 20. The reader 10 wirelessly communicates with the transponders 14, 16 to extracutaneously determine changes in the length of the leg 23.

The reader 10 and the transponders 14, 16 communicate through the bone fragments 18, 20, the patient's skin 26, and other tissues to measure a distance, D, between the transponders 14, 16. An increase in the distance, D, corresponds to an increase in the length of the bone 22 and thus the leg 23. The reader 10 indicates changes in length on a user interface 50 and communicates with one or more computer systems 30 over a network 28, which can be wired or wireless. The reader 10 can thus provide information indicating change in the length of the leg 23 to the patient and to medical professionals.

Figure 2:
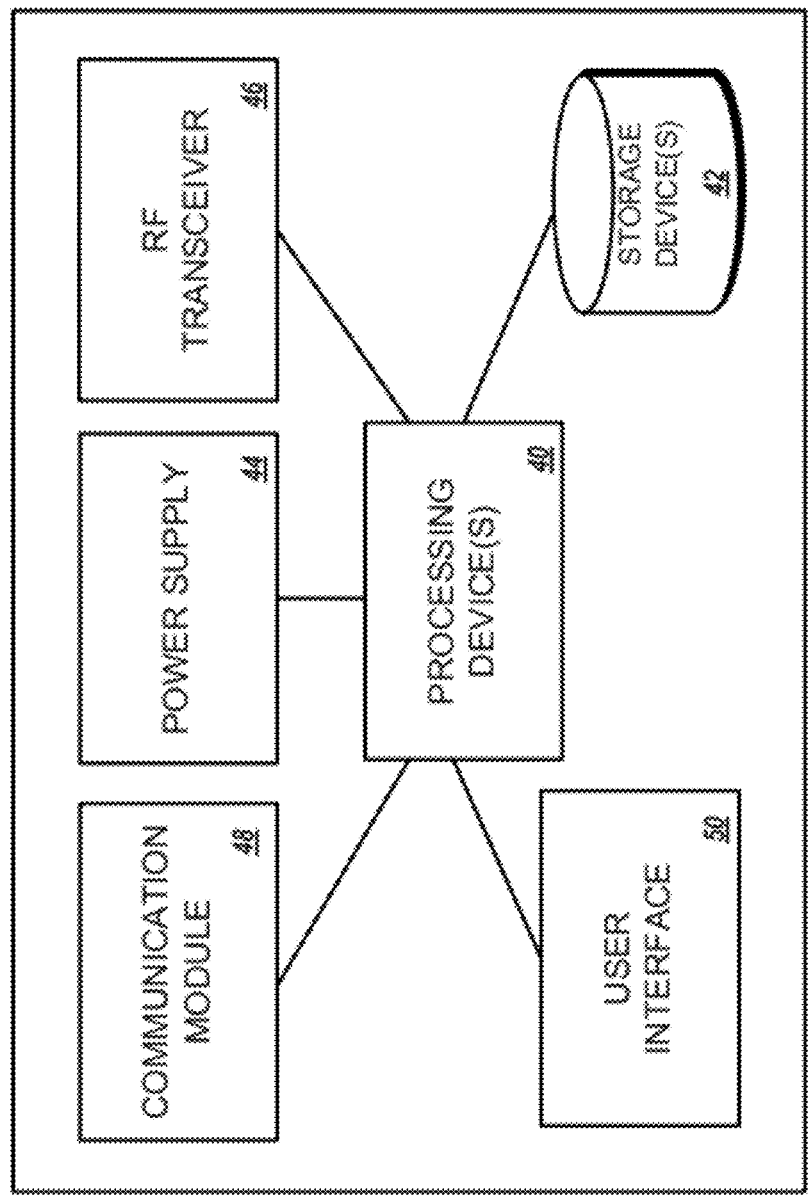
FIG. 2 is a block diagram of a reader of the system.

Referring to FIG. 2, the reader 10 is a handheld device, for example, a cellular phone, that includes an RF transceiver 46 operable to read RFID tags. In some implementations, the reader 10 includes a cellular phone and a removable attachment that includes the RF transceiver 46. The reader 10 can include a system of devices in communication with each other, which may not all be handheld. For example, the reader 10 can include a handheld wand that houses the RF transceiver 46 while other functions are performed by a computer system in communication with the wand.

The reader 10 includes one or more processing devices 40, one or more storage devices 42, and a power supply 44, which can include a rechargeable battery. The one or more storage devices 42 store data measured by the reader 10. The storage devices 42 also store instructions that are executed by the one or more processing devices 40, causing the one or more processing devices 40 to perform operations to control other components of the reader 10.

The reader 10 includes a communication module 48 and the user interface 50. The communication module 48 transmits and receives data over the network 28. In some implementations, the communication module 48 includes a transceiver capable of communicating over a cellular phone network. The user interface 50 includes a display for presenting information to a user of the reader 10, for example, a patient or a physician. The screen can be touch-sensitive to receive input from the user. The user interface 50 can include physical controls in addition to on-screen controls.

Figure 3:
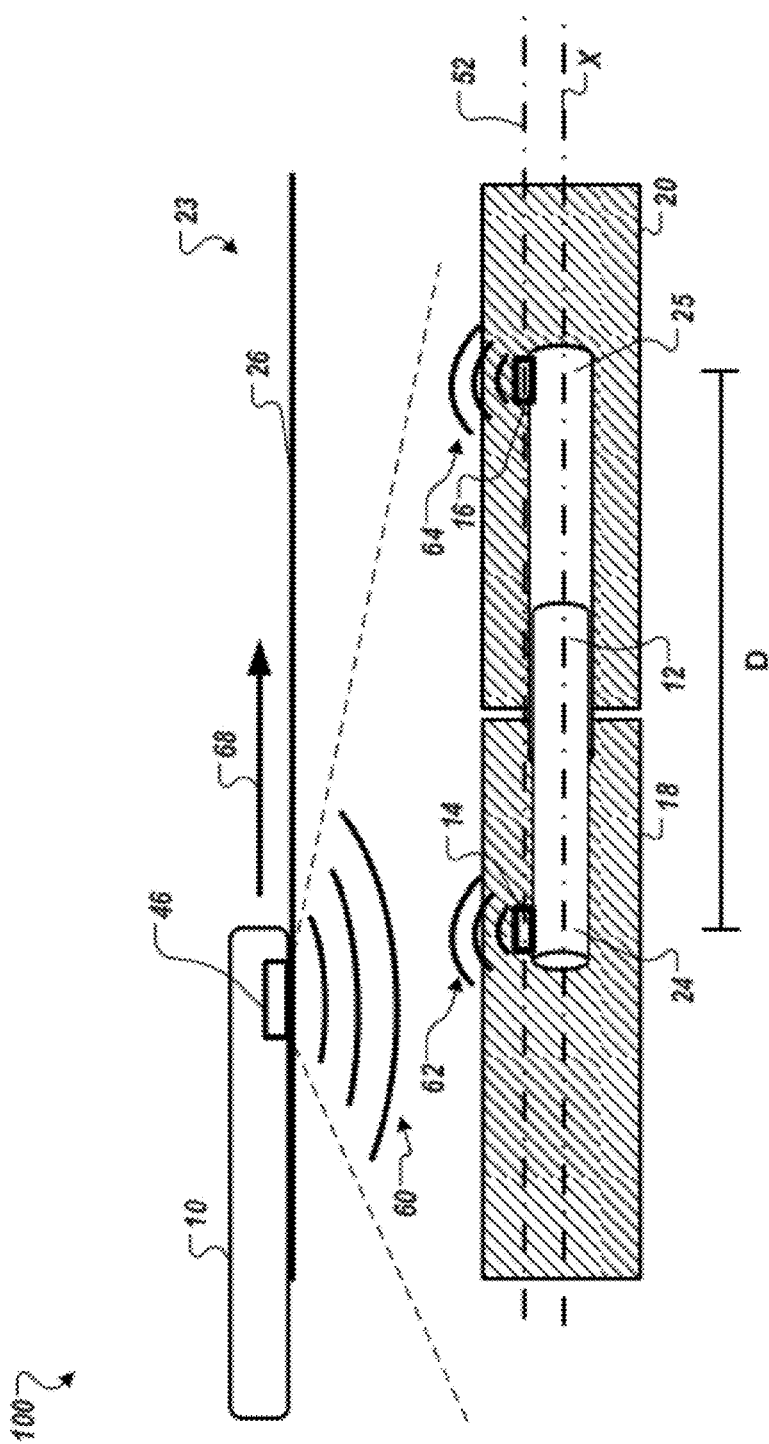
FIGS. 3, 4A, and 4C are side cutaway views illustrating the system.

Referring to FIG. 3, the reader 10 is used to measure the distance, D, between the transponders 14, 16. The transponders 14, 16 are passive RFID tags. Alternatively, the transponders 14, 16 can be active or semi-active RFID tags. The signals produced by the transponders 14, 16 can have a frequency within a range between about 30 kHz and 3 GHz including, for example, low-frequency (30 kHz to 300 kHz), high-frequency (3 MHz to 30 MHz), or ultra-high-frequency (300 MHz to 3 GHz) signals.

The transponders 14, 16 can be selected for high performance when mounted on metal or embedded in metal, for example, one of the PicoX II, Pico-iN, or Nano-iN series RFID tags manufactured by Xerafy, permitting the transponders 14, 16 to operate efficiently when mounted on a metal nail. In some implementations, the transponders are printed chipless RFID tags. The transponders 14, 16 can be autoclavable and/or tolerant of gamma radiation to permit sterilization. Examples include GammaTag 500 series RFID tags manufactured by AdvantaPure, µ-chip RFID tags manufactured by Hitachi, and the MicroX II RFID tags manufactured by Xerafy.

The transponders 14, 16, are also selected to have signal transmission and reception characteristics to accommodate a variety of patients. The transponders 14,16 have a read range sufficient large to transmit signals through soft tissue at a depth of, for example, 8 inches, 16 inches, 24 inches, or more. Thus the system 100 can effectively measure increases in bone length for patients having limbs of all sizes, including patients having with above-average limb diameters due to large quantities of muscle or adipose tissue.

The transponders 14, 16 are also selected to include bio-compatible materials and to have a small size to limit tissue irritation. For example, the transponders 14, 16, can be sufficiently small to be located within the nail 12. Alternatively, the transponders 14, 16, may be mounted on the exterior of the nail 12, with a size and thickness that results in limited irritation to surrounding tissue.

The transponders 14, 16 are selected to have matching operating characteristics. For example, the transponders 14, 16 have substantially the same latency between receiving an interrogation signal and transmitting a response signal. The transponders 14, 16 transmit response signals that encode different identifiers, permitting the reader 10 to distinguish the response signals from the different transponders 14, 16.

The transponders 14, 16 are oriented in a plane generally parallel to the longitudinal axis of the nail 12 with a common linear axis 52 of the transponders 14, 16 that is substantially parallel to the longitudinal axis, X, of the nail 12. The transponders 14, 16 can alternatively be oriented at a different position with respect to each other and with respect to the nail 12 and the bone fragments 18, 20, and offsets between the transponders 14, 16 can be input to the reader 10 to correct distance measurements.

The transponders 14, 16 are attached to different portions 24, 25 of the nail 12, spanning a fracture of the bone 22. The transponders 14, 16 can be coupled to the nail 12 by adhesive, or can be inlaid or mounted on the surface of the nail 12. In some implementations, the transponders 14, 16 are located within the different portions 24, 25 of the nail 12, for example, the transponders 14, 16, can reside in the nail within a pocket filled with potting material. The transponders 14, 16, can be encased in glass or plastic to protect them from bodily fluids.

To implant the nail 12, a surgeon creates an incision in the leg 23, fractures the bone 22 to create the bone fragments 18, 20, and implants the nail 12 in the intramedullary cavity of the bone fragments 18, 20. The nail 12 is provided to the surgeon with the transponders 14, 16 attached, as a sterilized assembly. Alternatively, the transponders 14, 16 can be affixed to the nail 12 by the surgeon prior to implanting the nail 12. Implantation of the nail 12 thus places the transponders 14, 16 in the intramedullary cavity of the bone fragments 18, 20. The nail 12 (or other bone-lengthening device) can include one, two, or more components. For example, the nail 12 can include two or more separate components that act against each other or through another mechanism to cause separation of the bone fragments 18, 20.

The portions 24, 25 move axially relative to each other to separate the bone fragments 18, 20, causing the bone 22 to be lengthened. In some implementations, the nail 12 is a telescoping intramedullary nail, such as a limb-lengthening nail. Other bone-lengthening devices, including those configured for subcutaneous placement or for external fixation, can alternatively be used. The nail 12 includes a mechanism that separates the portions 24, 25 by, for example, magnetic force, hydraulic force, shape memory, or a motor and gears. Movement of the portions 24, 25 relative to each other causes the transponders 14, 16 to move relative to each other by a corresponding amount.

Relative movement of the bone fragments 18, 20 does not require both bone fragments 18, 20 to be displaced during a lengthening procedure. For instance, over the course of distraction osteogenesis, one bone fragment 20 can be moved while the other bone fragment 18 is maintained substantially in its initial position with respect to the patient's anatomy. When one of the bone fragments 18, 20 remains stationary, the corresponding transponder 14, 16 will also remain stationary.

To measure a length of the bone 22, the user of the reader 10 selects a control of the user interface 50, causing the reader 10 to enter an acquisition mode in which the reader 10 can communicate with the transponders 14, 16. In the acquisition mode, the RF transceiver 46 periodically transmits an interrogation signal 60 and detects RF signals.

The user places the reader 10 in contact with the skin 26 and moves the reader 10 along the leg 23, in the direction of arrow 68. The reader 10 is placed substantially flat against the skin 26, and while contact with the skin 26 is maintained, the reader 10 is moved in a substantially linear direction 68, substantially parallel to the leg 23. Moving the reader 10 substantially parallel to the leg 23 moves the reader 10 in the direction 68 that is substantially parallel to the axis 52 defined by the transponders 14, 16.

The reader 10 transmits an interrogation signal 60 directed into the leg 23. The interrogation signal 60 propagates through an area sufficiently wide that, from a single position of the reader 10 relative to the transponders 14, 16, a single transmission of the interrogation signal 60 reaches both transponders 14, 16. The interrogation signal 60 reaches the transponders 14, 16 with sufficient energy to cause the transponders 14, 16 to produce signals that the reader 10 can detect and identify.

In response to the interrogation signal 60, each transponder 14, 16 transmits a response signal 62, 64. The RF transceiver 46 detects the signals 62, 64, and the reader 10 calculates the delay between the transmission of the interrogation signal 60 and detection of each response signal 62, 64.

In the illustration, the distance between the transponder 14 and the reader 10 is shorter than the distance between the transponder 16 and the reader 10. As a result, the delay between transmitting the interrogation signal 60 and detecting the response signal 62 is shorter than the delay between transmitting the interrogation signal 60 and detecting the response signal 64.

Figure 4A:
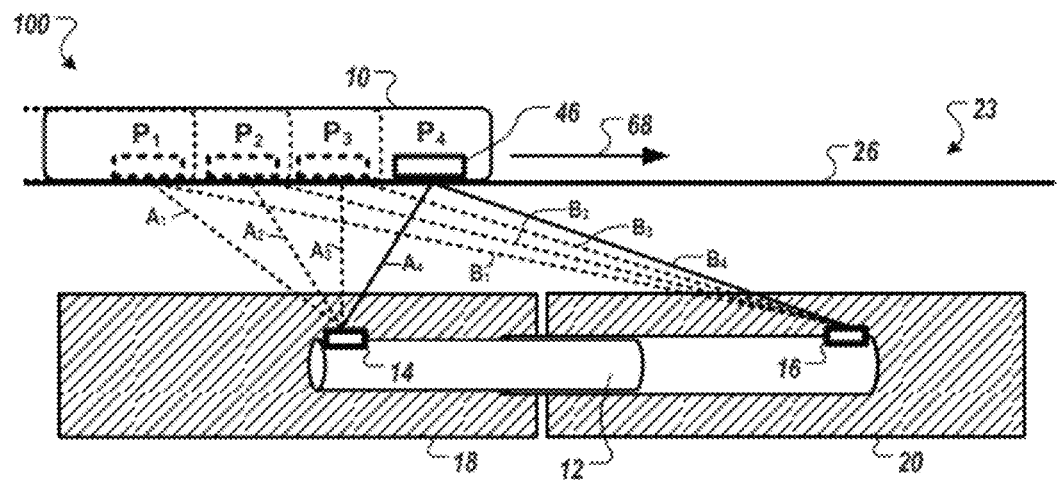

Referring to FIG. 4A, the RF transceiver 46 periodically transmits the interrogation signal 60 while the user moves the reader 10 along the leg 23, resulting in the interrogation signal 60 being transmitted from multiple locations relative to the transponders 14, 16. The RF transceiver 46 transmits the interrogation signal 60 at a high rate, permitting the reader 10 to perform measurements at a high sampling rate. In some implementations, transmissions of the interrogation signal 60 occur at a rate of greater than 200 Hz, for example, at a rate between 5 kHz and 1 MHz.

Transmissions of the interrogation signal 60 occur at multiple positions along the path of the reader 10, though only four positions, $P_1$-$P_4$, are illustrated for simplicity. Each position, $P_1$-$P_4$, indicates a location of the RF transceiver 46 from which the interrogation signal 60 is transmitted.

For each transmission of the interrogation signal 60 (for example, at each position, $P_1$-$P_4$), the reader 10 detects two corresponding response signals 62, 64, one from each transponder 14, 16. The reader 10 measures and records the delay between transmission of the interrogation signal 60 and detection of each corresponding response signal 62, 64. The reader 10 also records data indicating that the two related delay measurements correspond to the same position, one of $P_1$-$P_4$. In other words, related delay measurements indicate delays of different response signals 62, 64 relative to the same transmission of the interrogation signal 60.

Due to the propagation speed of the signals 60, 62, 64, movement of the reader 10 caused by the user does not practically affect the delay measurements. For example, for the transmission of the interrogation signal 60 from the position, $P_1$, the corresponding response signals 62, 64 reach the RF transceiver 46 practically at the position $P_1$.

Figure 4B:
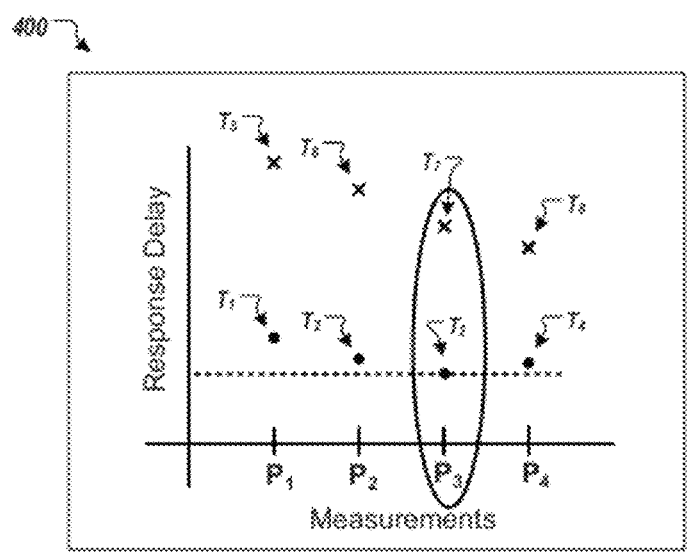
FIG. 4B is a diagram illustrating example data measured by the system.

Referring also to FIG. 4B, response delays, $T_1$-$T_8$, measured by the reader 10 are illustrated on a diagram 400. As the reader 10 moves relative to the transponders 14, 16, the distance between the reader 10 and the transponders 14, 16 varies. Because the distances traveled by the interrogation signal 60 and the response signals 62, 64 are different for different positions, $P_1$-$P_4$, the response delays, $T_1$-$T_8$, for the positions, $P_1$-$P_4$, are different. The duration of each time delay, $T_1$-$T_8$, is correlated to the length of the distance traveled by the interrogation signal 60 and the response signal 62, 64.

The delays $T_1$-$T_4$ represent delays for response signals 62 transmitted by the first transponder 14, which travel over distances, $A_1$-$A_4$, respectively. The delays $T_5$-$T_8$ represent delays for response signals 64 transmitted by the second transponder 16, which travel over distances, $B_1$-$B_4$, respectively. Each position, $P_1$-$P_4$, has a corresponding pair of delays (e.g., $T_1$ and $T_5$; $T_2$ and $T_6$; $T_3$ and $T_7$; and $T_4$ and $T_8$) indicating the delays between transmission of the interrogation signal 60 at that position, $P_1$-$P_4$, and detection of the corresponding response signals, 62, 64.

The reader 10 identifies the shortest response delay out of all of the measured delays, $T_1$-$T_4$, between transmission of the interrogation signal 60 and detection of the corresponding response signal 62 transmitted by the first transponder 14. In the illustrated example, the shortest delay is the delay, $T_3$. The reader 10 also identifies the other delay, $T_7$, corresponding to the same position, $P_3$. The delay, $T_7$, is related to the shortest delay, T3, in that both delays, $T_3$, $T_7$, indicate intervals between a single transmission of the interrogation signal 60 and detection of a response signal 62, 64 transmitted in response to that transmission.

Figure 4C:
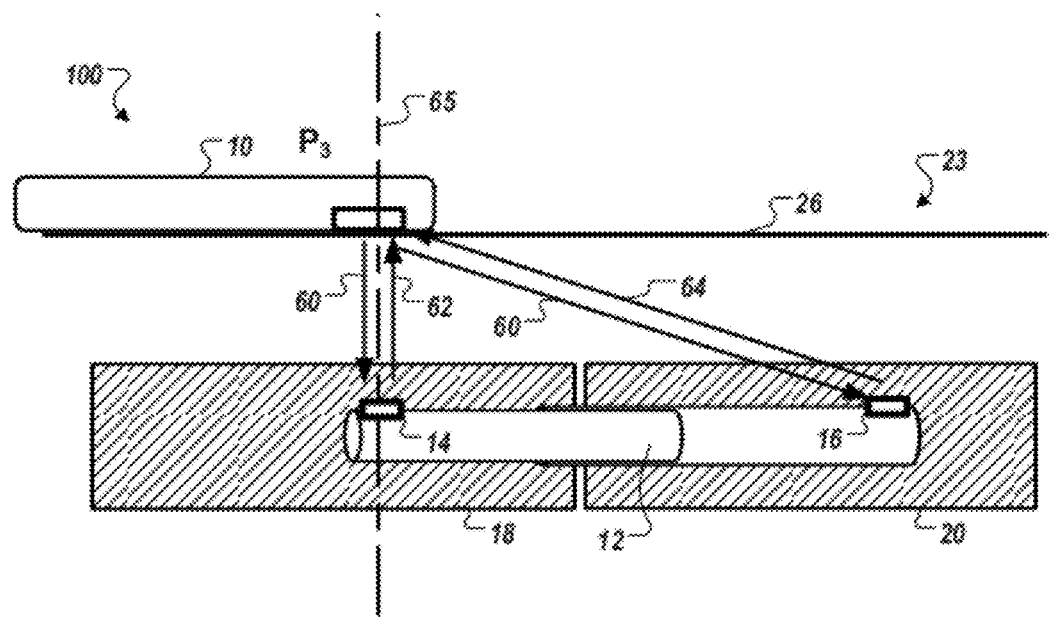
Figure 4D:
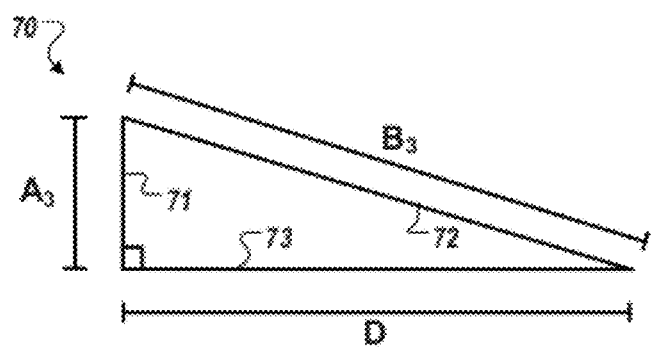
FIG. 4D is a diagram illustrating an example of calculation of a distance.

Referring to FIGS. 4C and 4D, the shortest response delay, $T_3$, corresponds to the measurement position at which the RF transceiver 46 is closest to the first transponder 14. At this position, $P_3$, an axis 65 through the RF transceiver 46 and the first transponder 14 is substantially perpendicular to the nail 12. Thus of all the positions, $P_1$-$P_4$, at which measurements occur, the position, $P_3$, is the position at which the distances between the RF transceiver 46, the first transponder 14, and the second transponder 16 most closely form a right triangle 70 (FIG. 4D). By considering the RF transceiver 46 and the transponders 14, 16 to be located at vertices of the right triangle 70, the reader 10 uses the measured delays, $T_3$, $T_7$, to triangulate the distance, D, between the transponders 14, 16.

The distances, $A_3$, $B_3$, between the RF transceiver 46 and the transponders 14, 16 can be determined using the measured time delays. Each measured delay, $T_3$, $T_7$, represents a time required for EM signals to traverse a distance twice: first, for the interrogation signal 60 from the RF transceiver 46 to reach one of the transponders 14, 16; and second, for the response signal 62, 64 from the transponder 14, 16 to reach the RF transceiver 46. Because the propagation speed of the EM signals 60, 62, 64 is known, that is, the EM signals propagate at the speed of light, the distances, $A_3$, $B_3$, can be calculated from the measured delays, $T_3$, $T_7$. The relationship between a distance, X, and a corresponding response delay, T, is indicated in Equation 1, below.

$$\text{Distance } X = \tfrac{1}{2} * C * T \quad \quad \text{Equation 1:}$$

where T is the delay between a transmission of an interrogation signal and detection of a corresponding response signal, and where C is the speed of light. The value for the speed of light, C, can be selected to reflect the speed of light in bodily tissue.

In some implementations, an adjusted delay, $T_{adj}$, is used in place of a measured delay, T. To calculate the adjusted delay, $T_{adj}$, delays that are not attributable to propagation of the signals are subtracted from the measured delay. For example, if the transponders 14, 16 incur a consistent latency between receiving the interrogation signal and transmitting a response signal, that latency can be subtracted from the measured delay to generate the adjusted delay, $T_{adj}$.

The distance, $A_3$, calculated using the shortest delay, $T_3$, represents one leg 71 of the triangle 70, and the distance, $B_3$, calculated using the related delay, $T_7$, represents the hypotenuse 72 of the triangle 70. The distance, D, between the transponders 14, 16 is the remaining leg 73 of the triangle 70. The distance, D, can be generated using, for example, the Pythagorean theorem and solving for the distance, D. For example, this relationship is indicated in Equation 2, below.

$$\text{Distance } D = \text{SQRT}[(\tfrac{1}{2} * C * T_L)^2 - (\tfrac{1}{2} * C * T_S)^2] \quad \text{Equation 2:}$$

where $T_S$ is the shortest measured time delay between transmission of an interrogation signal and detection of a response signal from a first transponder, and $T_L$ is the measured time delay between the same transmission of the interrogation signal and detection of a response signal from the other transponder. As described above, in some implementations, adjusted delays are used rather than measured delays.

The reader 10 calculates a distance spanned by the transponders 14, 16, for example, the entire distance between the transponders 14, 16, such as the distance, D, or a portion of the distance spanned by the transponders 14, 16, such as a distance that represents an increase in separation of the transponders 14, 16. The reader 10 calculates the distance, D, between the transponders 14, 16, and records the calculated distance with the date and time that the measurement occurred. The reader 10 also accesses data indicating previous measurements and determines a change in the length of the leg 23. The change in leg length is indicated by the increase in separation between the transponders 14, 16, which the reader 10 calculates by subtracting a previously measured distance between the transponders 14, 16 from the currently measured distance, D. The reader 10 calculates the change in the length of the leg 23 with respect to, for example, the most recent measurement, or a measurement that occurred at a particular time, such as approximately 24 hours ago.

The reader 10 also calculates a change in the length of the leg 23 since an initial baseline measurement was made, thus determining the cumulative change in the length of the leg. After surgery to implant the nail 12, a surgeon measures the distance, D, by moving the reader 10 along the outside of the skin 26, as described above. For example, the surgeon can demonstrate how to use the reader 10, while establishing a baseline distance, D, between the transponders 14, 16. In addition, a baseline length of the bone 22 or the leg 23 can be separately measured with other instruments. The baseline leg length is entered on the reader 10 along with other parameters, such as the prescribed rate of bone lengthening and the final target length of the leg 23. Increases in the distance, D, from the baseline distance thus indicate corresponding increases in the length of the leg 23 from the baseline leg length.

In some implementations, the user measures the distance, D, by moving the reader 10 along the entire length of the nail 12. As a result, the reader 10 measures response delays for a position where the RF transceiver 46 is located substantially over the first transponder 14 and for a position where the RF transceiver 46 is located substantially over the second transponder 46. The reader 10 calculates the distance, D, using the shortest delay for a response signal 62 from the first transponder 14 and its related delay. The reader 10 also calculates the distance, D, a second time using the shortest delay for a response signal 64 from the transponder 16 and its related delay. This second calculation uses measurements corresponding to the position where the RF transceiver 46 is closest to the second transponder 16. The reader 10 compares the two calculated distances and determines whether they are within a tolerance of each other. For example, the reader 10 subtracts one calculated distance from the other and compares the difference to a threshold. If the difference does not satisfy the threshold, the reader 10 visibly or audibly indicates that the user should move the reader 10 past the transponders 14, 16 again to acquire new measurement data.

In some implementations, the reader 10 includes a pressure sensor configured to sense pressure against the side of the reader 10 that contacts the patient's skin 26. At various times during movement along the patient's skin 26, the reader 10 measures a pressure exerted against the reader 10. Large variations in pressure can indicate a non-uniform path of the reader 10, which may in turn reduce the accuracy of measurements in some instances. The reader 10 can compare multiple pressures measured at different times while data is acquired by the reader 10. When the difference between the measured pressures exceeds a threshold, the reader 10 can produce an alarm or indicate on the user interface 50 that new data should be acquired. In addition, while data is acquired, information may be displayed on the user interface 50 to indicate the pressure against the reader 10, assisting the user to move the reader 10 with a generally consistent pressure along the skin 26.

Referring to FIG. 5, after the user measures the distance, D, the reader 10 provides information to the user on the user interface 50. The reader 10 displays the change in length 74 since the previous measurement. The reader 10 displays cumulative lengthening 75 of the leg 23 since the lengthening process began. The reader 10 can also calculate and display the change in length over a period of time, for example, by hour, by day, or by week. The reader 10 can also display the remaining distance 76 to be lengthened to complete the lengthening procedure. In some implementations, the reader 10 calculates the current length of the leg 23, for example by adding the cumulative change in length 74 to the baseline length of the leg 23, and the reader 10 calculates the leg length on the user interface 50. In some implementations, the reader 10 provides some or all of this information to the user through an e-mail message or a Short Message Service (SMS) text message.

The reader 10 also displays a reminder 77 indicating when a measurement is scheduled or when adjustment of the nail 12 or other lengthening device is scheduled. The reader 10 can also provide a reminder by e-mail or text message. The reader 10 can display instructions to the user that indicate when measurements should occur, and can indicate when measurements were not performed as scheduled. When the time for a scheduled measurement arrives, or at various intervals after a measurement is missed, the reader 10 provides a visible, audible, or tactile alarm.

The reader 10 also compares the change in the distance, D, over a period of time to the amount of lengthening prescribed for the patient for that period of time. When the reader 10 determines that the amount of lengthening does not satisfy a threshold (e.g., the lengthened amount is outside of a target range), the reader provides a warning or an alarm. For example, leg lengthening may be prescribed for a rate of one millimeter per day, with a tolerance of 0.25 millimeters. If the reader 10 determines that lengthening over the previous day is more than an upper threshold of 1.25 millimeters, the reader 10 provides an alarm indicating the excessive lengthening. Similarly, if the change in length is less than a lower threshold of 0.75 millimeters, the reader 10 can provide an alarm that indicates that lengthening is insufficient. In some implementations, alarm messages can also be transmitted to medical personnel. In some implementations, the reader 10 also displays instructions to the user to restore the separation rate to the target range, for example, instructions to adjust the nail 12 or to visit a physician.

In some implementations, the reader 10 transmits information indicating leg length calculations to the computer system 30 over the network 28 (FIG. 1). The computer system 30 can be a server system that stores received length measurements and provides access to the distance measurements to the patient and the patient's physician. The reader 10 or the computer system 30 can also transmit messages to medical personnel to indicate the amount of lengthening that has occurred. The reader 10 can send a message indicating any of the alarms or warnings that are provided to the patient.

Figure 6:
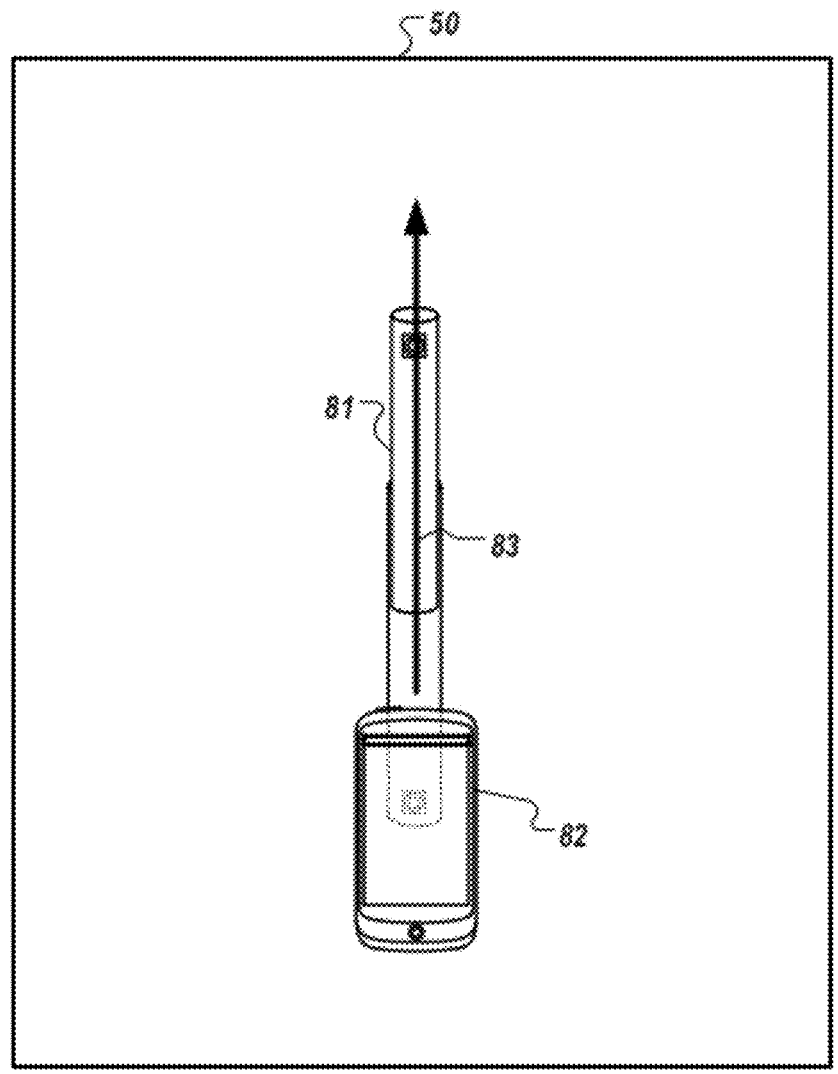
FIG. 6 is diagram illustrating another user interface of the reader.

Referring to FIG. 6, the reader 10 displays on the user interface 50 instructions indicating how to perform a measurement using the reader 10. The reader 10 displays illustrations, such as images, icons, or video, indicating actions the user should perform to take a measurement. The reader 10 displays an image 81 of the nail 12, an image 82 of the reader 10, and an indication 83 of the path that the user should move the reader 10 to record a measurement.

Because the reader 10 measures skeletal distraction by directly measuring the distance, D, between the transponders 14, 16, the reader 10 can measure changes in length when different mechanisms are used to separate the bone fragments 18, 20. The measurements can be made whether separation is caused by devices internal or external to the patient.

Figure 7:
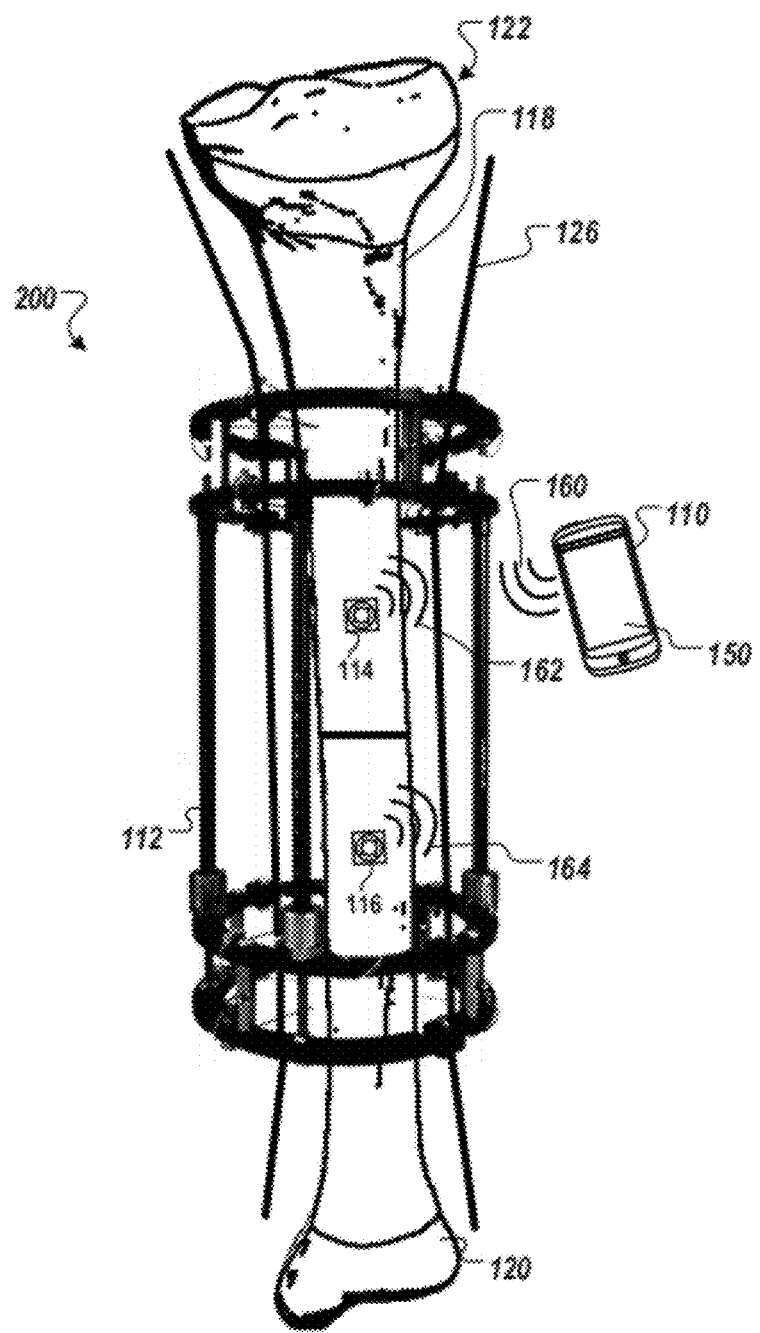
FIG. 7 is a perspective cutaway view of an alternative system for measuring skeletal distraction.

Referring to FIG. 7, rather than employing a telescoping nail, a system 200 for measuring skeletal distraction includes a reader 110, two transponders 114, 116, and an external fixation device 112. The transponders 114, 116 are attached directly to different bone fragments 118, 120 of a bone 122, and are arranged to move with their respective bone fragments 118, 120. The reader 110 communicates with the transponders 114, 116 in the same manner described above for the reader 10 and transponders 14, 16, by transmitting an interrogation signal 160 while the reader 110 moved along the patient's skin 126 and detecting response signals 162, 164 from the transponders 114, 116.

The external fixation device 112 can be a circular fixation device, for example, a frame that surrounds a limb. Alternatively, the external fixation device 112 can be a monolateral fixation device including a bar or other component positioned along the bone 122. Other external fixation devices can also be used.

In some implementations, the reader 110 is attached to the external fixation device 112. The reader 110, or components of the reader 110 such as an RF transceiver, can be slidably mounted on one or more struts or rails of the external fixation device 112. The reader 110 can be coupled to a motorized transference unit of the external fixation device 112 configured to slide the reader 110 against the patient's skin 126. The reader 110 and the transference unit can be programmed to, at various times each day, slide the reader 110 along the skin 126 along the bone fragments 118, 120 while communicating with the transponders 114, 116. Calculated distances based on the measurements performed can be communicated visually on a user interface, audibly, or over a network.

To begin the lengthening process, a surgeon creates an incision to access the bone 122 and preforms an osteotomy to break the bone 122 into the bone fragments 118, 120. The surgeon then attaches one of the transponders 114, 116 to each of the bone fragments 118, 120. The transponders 114, 116 are attached, each to a bone anchoring device such as a threaded housing, and the surgeon screws the housing for each transponder 114, 116 into the corresponding bone fragment 118, 120. The surgeon then closes the incision.

In some implementations, the patient manually increases the separation of the bone fragments 118, 120 in increments, for example, in four adjustments each day of 0.25 millimeters each. The reader 110 reminds the patient when adjustments to the external fixation device 112 are needed by producing an alarm. After each adjustment, the patient uses the reader 110 to measure the distance between the transponders 114, 116.

The patient selects a control of the reader 110 causing the reader 110 to periodically transmit a wireless interrogation signal 160. The patient places the reader 110 in contact with the skin 126, and while the reader 110 periodically transmits the wireless interrogation signal 160, the patient moves the reader 110 relative to the first bone fragment 118 and the second bone fragment 120. The transponders 114, 116 are located along an axis substantially parallel to the longitudinal axis of the bone 122, and the patient moves the reader 110 in a substantially linear direction, substantially parallel to the longitudinal axis of the bone 122.

At each of multiple locations, the interrogation signal 160 is received by the first transponder 114 and the second transponder 116, and signals 162, 164 produced by the first transponder 114 and the second transponder 116 in response to the interrogation signal 160 are detected by the reader 110.

By measuring changes in length with the reader 110, a history of lengthening is recorded and is provided to the patient and medical personnel. Measurements by the reader 110 can be more accurate than distances indicated by the external fixation device 112 because the reader 110 measures the increases in length directly rather than indirectly. Measurements using the reader 110 can be used to verify the accuracy of distances indicated by the external fixation device 112.

Figure 8:
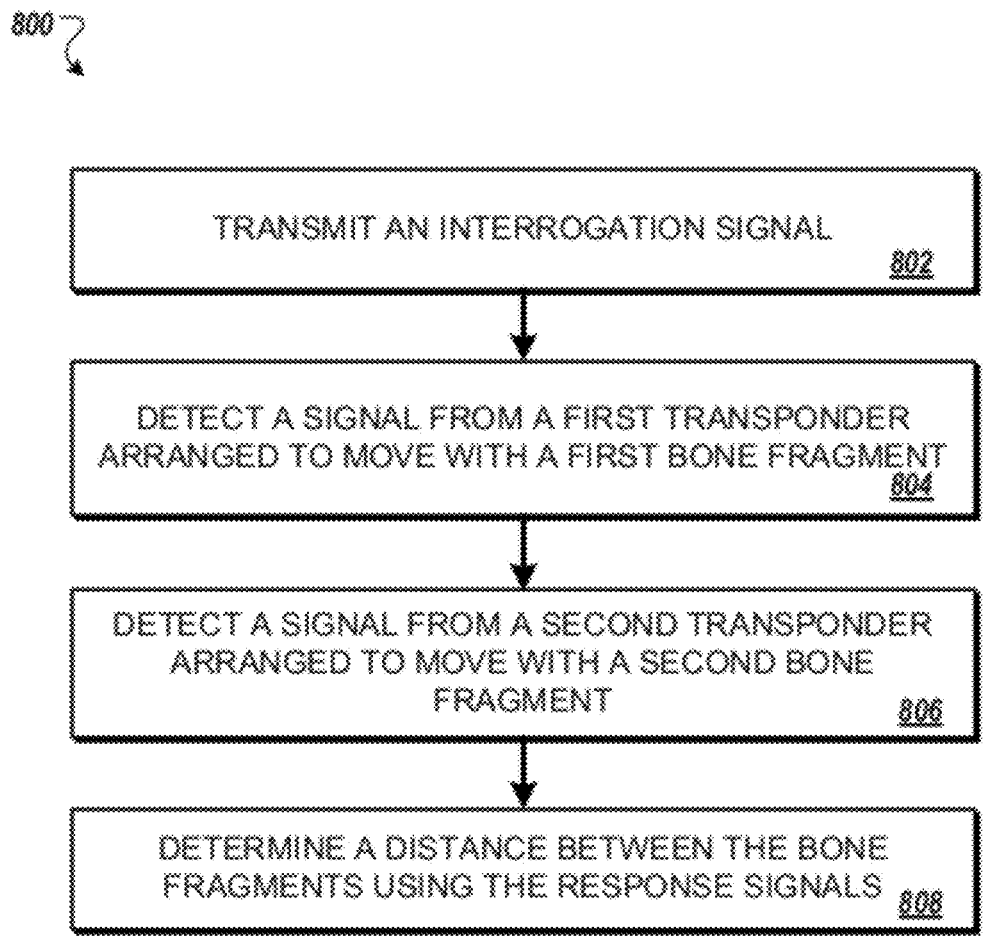
FIG. 8 is a flowchart illustrating a method of measuring skeletal distraction.

Referring to FIG. 8, a reader performs a process 800 for measuring skeletal distraction.

An interrogation signal is transmitted (802). The signal can be transmitted by an extracutaneous device, such as a cellular phone, while in contact with the skin of the patient.

A first signal transmitted in response to the interrogation signal is detected (804). The first signal is transmitted by a first transponder arranged to move with a first bone fragment. A second signal transmitted in response to the interrogation signal is detected (806). The second signal is transmitted by a second transponder arranged to move with a second bone fragment.

The first transponder and the second transponder can be passive RFID tags. The first transponder and the second transponder can be located in the intramedullary cavity of their respective bone fragments. The transponders can be attached to a subcutaneous bone-lengthening device such as an intramedullary nail.

A distance between the bone fragments is determined using the response signals (808). The reader measures a first delay between transmitting the interrogation signal and detecting the first signal. The reader measures a second delay between transmitting the interrogation signal and detecting the second signal. The reader calculates a distance between the bone fragments by determining a length based on the first delay and a length based on the second delay, and calculating the distance as a leg of a right triangle including the lengths. The reader can determine the distance between the transponders, which can be used to determine an overall length of a bone or limb, or a change in length occurring between the transponders.

In some implementations, the interrogation signal is transmitted at each of a plurality of locations. The transmission of the interrogation signal can be performed by an extracutaneous device while the extracutaneous device is moved relative to the first bone fragment and the second bone fragment.

For each transmission of the interrogation signal, a corresponding first response signal from the first transponder and a corresponding second response signal from the second transponder are received. Calculating the distance between the bone fragments can include measuring delays between each transmission of the interrogation signal and detection of the corresponding first response signal and identifying a shortest delay of the measured delays. A related delay is also determined between the transmission of the interrogation signal that resulted in the shortest delay and detection of the corresponding second response signal. The distance between the bone fragments is calculated using the shortest delay and the related delay.

The process 800 can also include accessing a stored distance, for example, a baseline distance between the transponders or a previous calculation of the distance. The reader determines a difference between the calculated distance and the stored distance, and indicates the difference on a user interface, for example, as a change in length of a bone.

The process 800 can also include storing the calculated difference with a time or date that the measurement occurred. The method can also include determining that the calculated distance does not satisfy a threshold, and in response, providing an alarm indicating that the threshold is not satisfied.

Implementations of the subject matter and the functional operations described in this specification, including the process 800, can be implemented in digital electronic circuitry, in tangibly-embodied computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, an operating system, or a combination of one or more of them.

A number of implementations and alternatives have been described. Nevertheless, it will be understood that various modifications may be made without departing from the spirit and scope of the disclosure. Accordingly, other implementations are within the scope of the disclosure.

What is claimed is:

1. A system, comprising:
    a bone-lengthening device;

a first transponder and a second transponder, the transponders being coupled to the bone-lengthening device and spaced apart from each other along a length of the bone-lengthening device, the transponders each being operable to transmit a radio-frequency signal in response to an interrogation signal; and a movable handheld reader comprising
- a radio-frequency transceiver operable to transmit a wireless interrogation signal and detect responsive signals from the first transponder and the second transponder,
- one or more processing devices, and
- one or more storage devices storing instructions that are operable, when executed by the one or more processing devices, to cause the movable handheld reader to perform operations including:
  - transmitting the wireless interrogation signal from the movable handheld reader at each of a plurality of positions with respect to the bone-lengthening device,
  - detecting response signals from the first transponder and the second transponder produced in response to the wireless interrogation signal transmitted from the movable handheld reader, comprising detecting, for each transmission of the wireless interrogation signal from the plurality of positions, (i) a corresponding first response signal from the first transponder, and (ii) a corresponding second response signal from the second transponder,
  - determining delays between the transmission of the wireless interrogation signal from the movable handheld reader and detection of the response signals from the first transponder and the second transponder by the movable handheld reader, and
  - determining a distance spanned by the transponders based on the delays comprising:
    - determining, for each transmission of the wireless interrogation signal, a first delay between the transmission of the wireless interrogation signal and detection of the corresponding first response signal from the first transponder;
    - identifying a shortest delay of the first delays;
    - determining a related delay between the transmission of the wireless interrogation signal that resulted in the shortest delay and detection of the corresponding second response signal; and
    - determining the distance spanned by the transponders based on the shortest delay and the related delay.

2. The system of claim 1, wherein the operations further comprise:
accessing a stored distance,
determining a difference between the determined distance and the stored distance, and
indicating the difference on a user interface provided on a display of the movable handheld reader.

3. The system of claim 1, wherein the bone-lengthening device is a telescoping intramedullary nail.

4. The system of claim 1, wherein the first transponder is a passive RFID tag and the second transponder is a passive RFID tag.

5. The system of claim 1, wherein the bone-lengthening device has a longitudinal axis, and the first transponder and the second transponder are attached to the bone-lengthening device at different locations spaced apart along the longitudinal axis of the bone-lengthening device.

6. The system of claim 1, wherein the movable handheld reader is a cellular phone.

7. The system of claim 1, wherein the operations further comprise storing the distance in association with a time or date that measurement of the distance occurred.

8. The system of claim 1, wherein the operations further comprise:
determining that the distance does not satisfy a threshold; and
in response to determining that the distance does not satisfy the threshold, providing an alarm.

9. The system of claim 1, wherein the operations further comprise determining, using the distance spanned by the transponders, (i) a change in length of a bone based on the distance spanned by the transponders or (ii) an amount of distraction of bone fragments that has occurred during a particular period of time.

10. The system of claim 1, wherein the bone-lengthening device has a first portion that is configured to move relative to a second portion of the bone-lengthening device, wherein the first transponder is fixed to the first portion of the bone lengthening device and the second transponder is fixed to the second portion of the bone lengthening device.

11. The system of claim 1, wherein the bone-lengthening device is an implant configured for subcutaneous implantation and wherein the first transponder and the second transponder are configured for subcutaneous implantation, and
wherein the movable handheld reader is an extracutaneous device configured to communicate the first transponder and the second transponder while the first transponder and the second transponder are subcutaneously implanted.

12. The system of claim 1, wherein the bone-lengthening device is an intramedullary nail, and the first transponder and the second transponder are arranged on the intramedullary nail for placement in an intramedullary cavity of a bone.

13. The system of claim 1,
wherein transmitting the wireless interrogation signal from the movable handheld reader comprises transmitting the wireless interrogation signal from the movable handheld reader at a plurality of locations along a path while the movable handheld reader is moving along the path relative to the bone lengthening device;
wherein detecting the response signals from the first transponder and the second transponder comprises detecting, by the movable handheld reader, response signals from the first transponder and the second transponder corresponding to each transmission of the wireless interrogation signal at the plurality of locations along the path; and
wherein determining a distance spanned by the transponders based on the delays comprises determining the distance spanned by the transponders using response signals corresponding to transmissions of the wireless interrogation signal at the plurality of locations along the path.

14. The system of claim 13, wherein the path is a substantially linear path.

15. The system of claim 1, wherein the movable handheld reader is configured to determine the distance spanned by the transponders based on the interactions of a single transceiver with the first transponder and the second transponder.

16. The system of claim 1, wherein the movable handheld reader comprises a pressure sensor configured to sense pressure against a side of the movable handheld reader, wherein the movable handheld reader is configured to measure pressures with the pressure sensor during placement and movement of the movable handheld reader while the movable handheld reader transmits the wireless interrogation signal, and wherein the movable handheld reader is configured to assess variations in the pressures measured while the movable handheld reader moves and transmits the wireless interrogation signal.

17. The system of claim 16, wherein the operations further comprise:

determining that a difference between the measured pressures exceeds a threshold; and in response to determining that the difference between the measured pressures exceeds the threshold, outputting, by the movable handheld reader, an alarm or an indication that new data should be acquired using the radio-frequency transceiver.

18. The system of claim 1, wherein the operations further comprise displaying a user interface on a display of the movable handheld reader that instructs a user to move the movable handheld reader along a path.

19. A system, comprising:

a bone-lengthening device;

a first transponder and a second transponder, the transponders being coupled to the bone-lengthening device and spaced apart from each other along a length of the bone-lengthening device, the transponders each being operable to transmit a radio-frequency signal in response to an interrogation signal; and a reader comprising a radio-frequency transceiver operable to transmit a wireless interrogation signal and detect responsive signals from the first transponder and the second transponder, one or more processing devices, and one or more storage devices storing instructions that are operable, when executed by the one or more processing devices, to cause the reader to perform operations including:

transmitting multiple transmissions of the wireless interrogation signal from the reader, each of the multiple transmissions of the wireless interrogation signal being transmitted with the reader located at a different location relative to the bone lengthening device, detecting, for each of the multiple transmissions of the wireless interrogation signal, a corresponding first response signal from the first transponder and a corresponding second response signal from the second transponder, determining, for each of the multiple transmissions of the wireless interrogation signal, a first delay between the transmission of the wireless interrogation signal and detection of the corresponding first response signal from the first transponder, identifying a shortest delay of the first delays, determining a related delay that is a delay between the transmission of the wireless interrogation signal that resulted in the shortest delay and detection of the corresponding second response signal, and determining a distance spanned by the transponders based on the shortest delay and the related delay.

* * * * *